(12) United States Patent
Marici et al.

(10) Patent No.: US 12,290,491 B2
(45) Date of Patent: May 6, 2025

(54) CLOSED SYSTEM STRESS RESISTANT MEMBRANE

(71) Applicant: Becton Dickinson and Company Limited, Dun Laoghaire (IE)

(72) Inventors: Paul Paia Marici, Piscataway, NJ (US); Shawn Ray Isaacson, Layton, UT (US); Andrew C. Farinella, Oradell, NJ (US); Mitchell Evan Gatesman, Morrisville, NC (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 201 days.

(21) Appl. No.: 15/868,123

(22) Filed: Jan. 11, 2018

(65) Prior Publication Data

US 2018/0193227 A1 Jul. 12, 2018

Related U.S. Application Data

(60) Provisional application No. 62/445,393, filed on Jan. 12, 2017.

(51) Int. Cl.
*A61J 1/20* (2006.01)
*A61J 1/14* (2023.01)
(Continued)

(52) U.S. Cl.
CPC .......... *A61J 1/2044* (2015.05); *A61J 1/1406* (2013.01); *A61J 1/201* (2015.05); *A61J 1/2048* (2015.05);
(Continued)

(58) Field of Classification Search
CPC ...... A61J 1/2096; A61J 1/1406; A61J 1/2044; A61J 1/2089; A61J 1/20–22; Y10S 604/905
See application file for complete search history.

(56) References Cited

U.S. PATENT DOCUMENTS 5,242,393 A * 9/1993 Brimhall ............... A61M 39/26
604/249
5,678,713 A * 10/1997 Derksen ................ A61J 1/1406
215/249
(Continued)

FOREIGN PATENT DOCUMENTS

CN 106232164 A 12/2016
EP 2739342 A0 6/2014
(Continued)

*Primary Examiner* — Andrew J Mensh
*Assistant Examiner* — Meagan Ngo
(74) *Attorney, Agent, or Firm* — The Webb Law Firm

(57) ABSTRACT

A membrane for use in connection with a closed system transfer device has a body with a proximal portion opposite a distal portion along a central axis and a skirt extending radially outward from the distal end such that a lip is formed at a transition between the proximal portion and the distal portion. The membrane further has at least one well recessed in a proximal direction from a distal end of the distal portion, thereby forming a channel within the distal portion having an open first end, a closed bottom end, and a pair of sidewalls extending between the first end and the second end. At least one slit extends through at least a portion of the body in a direction of a plane aligned along or parallel to the central axis.

25 Claims, 16 Drawing Sheets

(51) Int. Cl.
    *A61M 5/14*     (2006.01)
    *A61M 5/162*     (2006.01)

(52) U.S. Cl.
    CPC .......... *A61J 1/2096* (2013.01); *A61M 5/1413* (2013.01); *A61J 1/20* (2013.01); *A61M 5/162* (2013.01)

(56) References Cited

U.S. PATENT DOCUMENTS

| | | | |
|---|---|---|---|
| 5,921,264 A * | 7/1999 | Paradis | A61M 39/045 137/15.17 |
| 6,030,582 A | 2/2000 | Levy | |
| 6,171,287 B1 | 1/2001 | Lynn et al. | |
| 8,523,838 B2 | 9/2013 | Tornqvist | |
| 9,808,401 B2 | 11/2017 | Ishiwata et al. | |
| 10,569,031 B2 | 2/2020 | Sullivan et al. | |
| 2002/0193752 A1 * | 12/2002 | Lynn | A61M 39/02 604/249 |
| 2005/0215943 A1 * | 9/2005 | Brandenburger | A61J 1/1406 604/30 |
| 2006/0184140 A1 * | 8/2006 | Okiyama | A61M 39/045 604/249 |
| 2011/0130740 A1 * | 6/2011 | Levy | A61J 1/05 604/403 |
| 2013/0299021 A1 * | 11/2013 | Gobbi Frattini | A61J 1/1475 137/624.27 |
| 2014/0150911 A1 | 6/2014 | Hanner et al. | |
| 2014/0150925 A1 | 6/2014 | Sjogren et al. | |
| 2014/0174578 A1 * | 6/2014 | Bonnal | A61J 1/2096 137/798 |
| 2014/0311617 A1 * | 10/2014 | Py | A61J 3/002 141/1 |
| 2015/0082746 A1 | 3/2015 | Ivosevic et al. | |
| 2015/0112296 A1 * | 4/2015 | Ishiwata | A61J 1/1406 604/406 |
| 2015/0297454 A1 | 10/2015 | Sanders et al. | |
| 2015/0297459 A1 * | 10/2015 | Sanders | A61J 1/2096 604/414 |
| 2015/0366758 A1 * | 12/2015 | Noguchi | A61J 1/2044 604/407 |
| 2017/0071826 A1 * | 3/2017 | Py | A61J 1/1406 |
| 2018/0064605 A1 * | 3/2018 | Noguchi | A61J 1/2006 |
| 2018/0263847 A1 * | 9/2018 | Kajihara | B65B 3/003 |

FOREIGN PATENT DOCUMENTS

| | | |
|---|---|---|
| JP | 2002-516160 A | 6/2002 |
| JP | 2003-522318 A | 7/2003 |
| WO | 2005004973 A1 | 1/2005 |
| WO | 2013/017698 A1 | 2/2013 |
| WO | 2013/179596 A1 | 5/2013 |
| WO | 2014046271 A1 | 3/2014 |
| WO | 2014/145313 A2 | 9/2014 |

\* cited by examiner

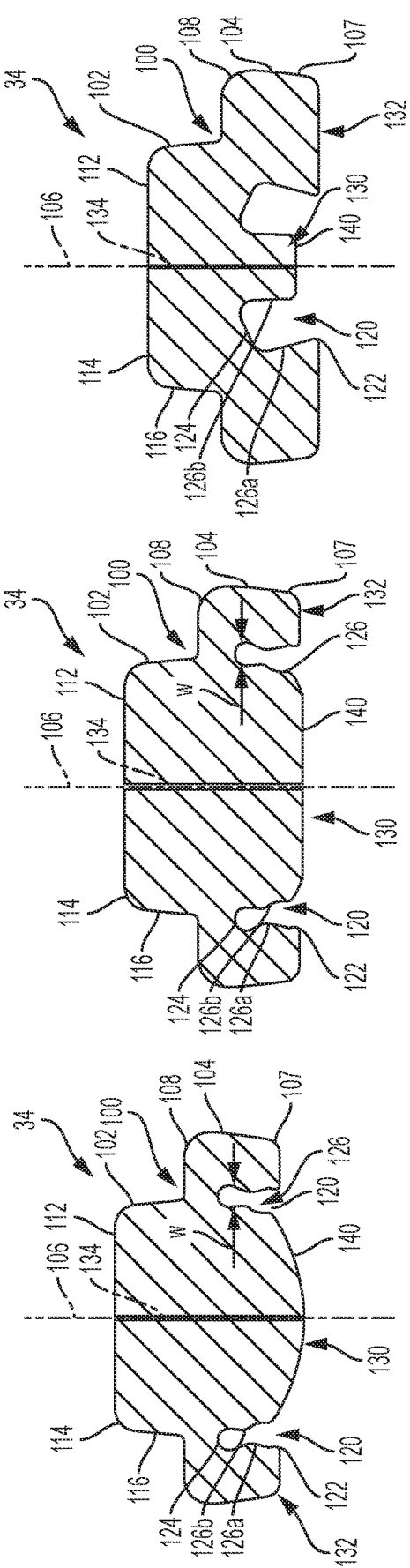
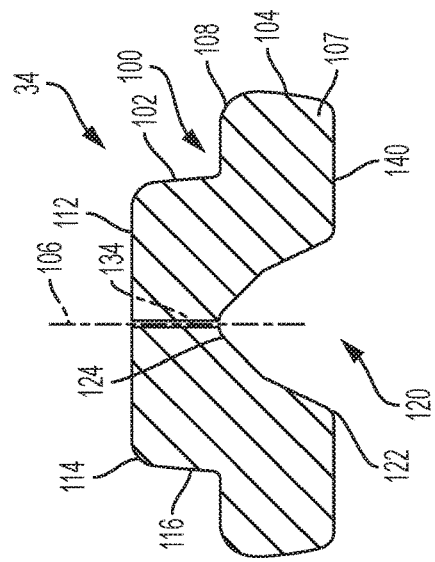
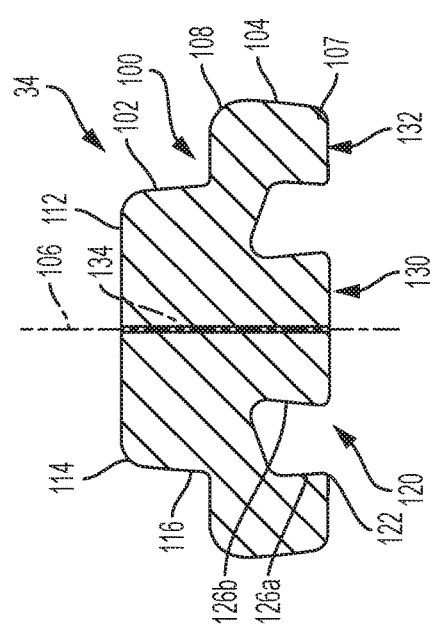
FIG. 7A
FIG. 7B
FIG. 7C
FIG. 7D
FIG. 7E

CLOSED SYSTEM STRESS RESISTANT MEMBRANE

CROSS-REFERENCE TO RELATED APPLICATION

This application claims priority to U.S. Provisional Application No. 62/445,393, filed Jan. 12, 2017, entitled "Closed System Stress Resistant Membrane", the entire disclosure of which is hereby incorporated by reference.

BACKGROUND OF THE INVENTION

1. Field of the Disclosure

The present disclosure relates generally to systems for closed system transfer of fluids. More particularly, the present disclosure relates to systems for closed transfer of fluids having stress resistant membranes that provide leak-proof sealing during fluid transfer from a first container or device to a second container or device.

2. Description of the Related Art

Health care providers reconstituting, transporting, and administering hazardous medications, such as cancer treatment medications, can put themselves at risk of exposure to these medications and present a major hazard in the health care environment. For example, nurses treating cancer patients risk being exposed to chemotherapy drugs and their toxic effects. Unintentional chemotherapy exposure can affect the nervous system, impair the reproductive system, and bring an increased risk of developing blood cancers in the future. In order to reduce the risk of health care providers being exposed to toxic drugs, a closed transfer of these drugs during reconstituting, transporting, and administering becomes important.

Some drugs must be dissolved or diluted before they are administered, which involves transferring a solvent from a first container to a second container, such as a sealed vial containing the drug in powder or liquid form, by means of a needle. Drugs may be inadvertently released into the atmosphere in gas form or by way of aerosolization, during the withdrawal of the needle from the vial and while the needle is inside the vial if any pressure differential between the interior of the vial and the surrounding atmosphere exists. It would be advantageous to provide a system for closed transfer of fluids that provide leak-proof sealing during fluid transfer from the first container to the second container.

SUMMARY OF THE INVENTION

The present disclosure provides a system for closed transfer of fluids from a first container to a second container. The system has a stress resistant membrane that provides a leak-proof sealing during fluid transfer from the first container to the second container.

In some examples, a membrane for use in connection with a closed system transfer device may have a body with a proximal portion opposite a distal portion along a central axis and a skirt extending radially outward from the distal portion such that a lip is formed at a transition between the proximal portion and the distal portion. The membrane further may have at least one well recessed in the distal portion and extending from a distal end of the distal portion in a proximal direction, thereby forming a channel within the distal portion. The channel may have an open first end, a closed bottom end, and a pair of sidewalls extending between the first end and the second end. At least one slit may extend through at least a portion of the body in a direction of a plane aligned along or parallel to the central axis.

In other examples, the at least one well may be continuous in a circumferential direction about the central axis. The at least one well may be discontinuous in a circumferential direction about the central axis. The at least one well may have an annular shape. The at least one well may have a plurality of wells with each well positioned at a different radius away from the central axis. The at least one well may have a plurality of wells positioned at a same radius away from the central axis and separated from each other by at least one connecting rib.

In other examples, the at least one slit may extend through at least a portion of the distal portion of the body in a direction along the central axis. The at least one slit may be configured to be opened by a cannula during penetration of the cannula through the membrane and to close upon withdrawal of the cannula from the membrane. The at least one slit may be positioned on a raised area that protrudes distally from the distal portion of the distal end. The raised area may be arcuately shaped with an apex at the central axis of the membrane. The at least one slit may be a pair of slits intersecting each other at a midpoint of each slit. The at least one slit may be three slits connected to one another at one of their end points. The slits may intersect at a perpendicular angle. The slits may be arranged such that the cannula penetrates the slits through an intersection point of the slits.

In other examples, a retention ring may protrude in a distal direction from the distal portion of the distal end. The retention ring may be continuous in a circumferential direction about the central axis. The retention ring may be discontinuous in a circumferential direction about the central axis. The retention ring may have an annular shape. The proximal portion and the distal portion may be monolithically formed together. The body may be symmetrical about the central axis. The lip may be substantially perpendicular to the central axis. A proximal end of the proximal portion may have a convex surface or a planar surface. A distal end of the distal portion may have a convex surface or a planar surface. An outer perimeter of the proximal portion may have a radiused edge.

In other examples, a system for closed transfer of fluids may have a syringe adapter including a housing having a first end and a second end, with the first end configured to be secured to a first container, a cannula having a first end and a second end, the second end positioned within the housing, and a membrane having a body with a proximal portion opposite a distal portion along a central axis and a skirt extending radially outward from the distal end such that a lip is formed at a transition between the proximal portion and the distal portion. The membrane may have at least one well recessed in a proximal direction from a distal end of the distal portion, thereby forming a channel within the distal portion having an open first end, a closed bottom end, and a pair of sidewalls extending between the first end and the second end. The membrane may have at least one slit extending through at least a portion of the body in a direction along the central axis. The system may further have a second component having a second membrane.

BRIEF DESCRIPTION OF THE DRAWINGS

The above-mentioned and other features and advantages of this disclosure, and the manner of attaining them, will become more apparent and the disclosure itself will be better understood by reference to the following descriptions of examples of the disclosure taken in conjunction with the accompanying drawings, wherein:

FIG. 7A is a cross-sectional side view of a stress resistant membrane in accordance with another example of the present invention.

FIG. 7B is a cross-sectional side view of a stress resistant membrane in accordance with another example of the present invention.

FIG. 7C is a cross-sectional side view of a stress resistant membrane in accordance with another example of the present invention.

FIG. 7D is a cross-sectional side view of a stress resistant membrane in accordance with another example of the present invention.

FIG. 7E is a cross-sectional side view of a stress resistant membrane in accordance with another example of the present invention.

Corresponding reference characters indicate corresponding parts throughout the several views. The exemplifications set out herein illustrate exemplary examples of the disclosure, and such exemplifications are not to be construed as limiting the scope of the disclosure in any manner.

DETAILED DESCRIPTION

Figure 1A:
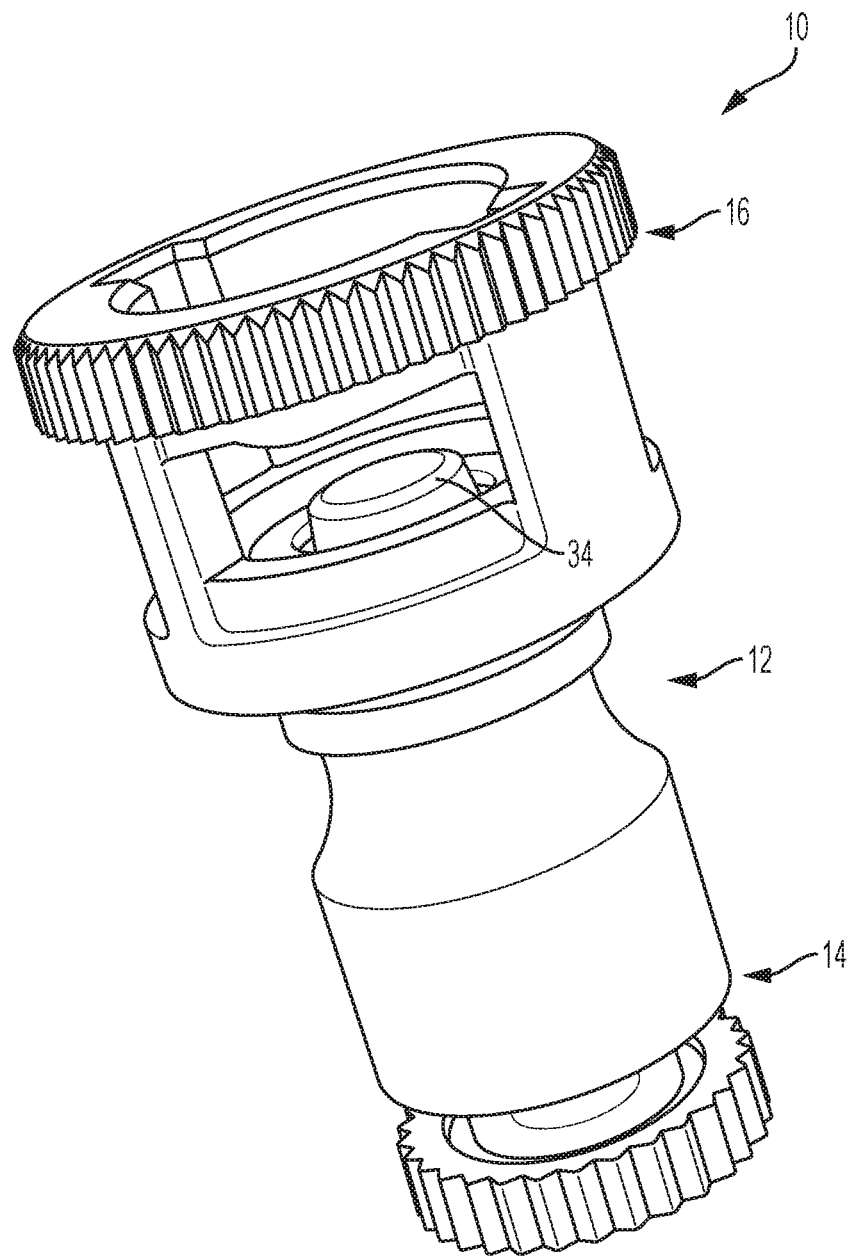
FIG. 1A is a perspective view of a system according to one example of the present invention.

The following description is provided to enable those skilled in the art to make and use the described examples contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary examples of the invention. Hence, specific dimensions and other physical characteristics related to the examples disclosed herein are not to be considered as limiting.

As used in the specification and the claims, the singular form of "a", "an", and "the" include plural referents unless the context clearly dictates otherwise.

Unless otherwise indicated, "proximal" shall refer to a part or direction located away or furthest from a patient and toward or closest to a clinician (upstream), while distal shall refer to a part or direction towards or located nearest to a patient and away or further from a clinician (downstream). Also, a drug substance is used herein in an illustrative, non-limiting manner to refer to any substance injectable into the body of a patient for any purpose. Reference to a patient may be to any being, human or animal. Reference to a clinician may be to any person or thing giving treatment, e.g., a nurse, doctor, machine intelligence, caregiver, or even self-treatment.

Unless otherwise indicated, all numbers expressing quantities used in the specification and/or claims are to be understood as modified in all instances by the term "about."

With reference to the FIGS. 1A-5B, the present disclosure is directed to various systems 10 for the closed transfer of fluids. In each example described herein with reference to FIGS. 1A-5B, the system 10 includes a stress resistant membrane that provides leak-proof sealing during fluid transfer from a first container or device to a second container or device. In each example, the system 10 provides substantially leak-proof sealing during transfer of a fluid from a first container or device, such as a vial, to a second container or device, such as a syringe, IV bag, or patient IV line. The leak-proof sealing of various examples of the system 10 substantially prevents leakage of both gas and liquid during use of the system 10.

Figure 1B:
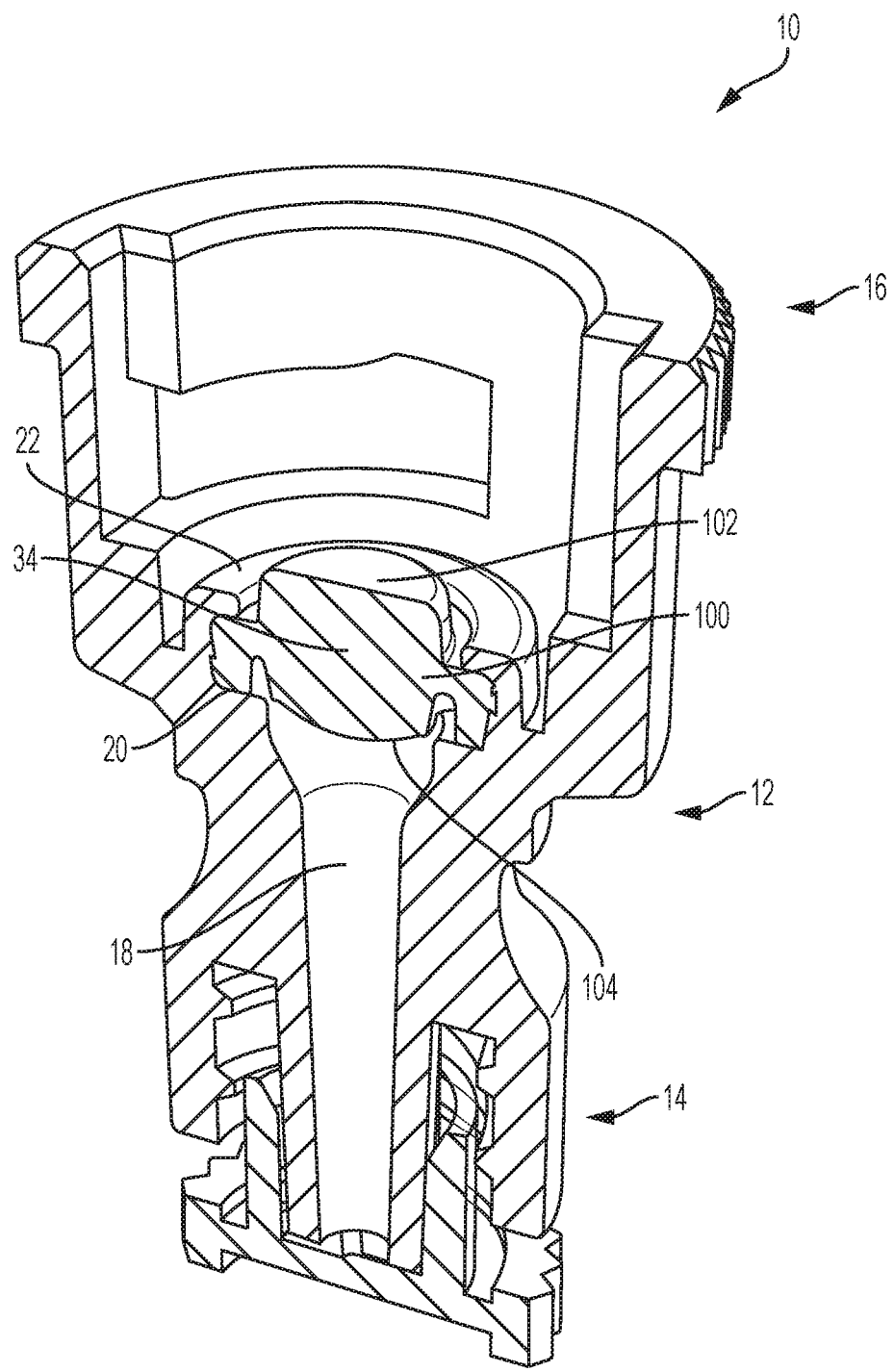
FIG. 1B is a perspective longitudinal cross-sectional view of the system shown in FIG. 1A.

Referring to FIGS. 1A-1B, one example of a system 10 for the closed transfer of fluids includes a connector 12 which provides a leak-proof seal throughout a drug transfer procedure. Various aspects of the connector 12 are described in U.S. Patent Application Publication No. 2014/0074038, which is hereby incorporated in reference in its entirety.

Referring to FIGS. 1A-1B, one example of the connector 12 is configured for connecting to an intravenous line (not shown) inserted into a bloodstream of a patient. In one embodiment, the connector 12 comprises a PhaSeal™ connector which is compatible with a Becton Dickinson PhaSeal™ System available from Becton, Dickinson and Company of Franklin Lakes, N.J. In other embodiments, the connector 12 comprises a connector which is compatible with other closed system drug transfer devices.

Figure 2:
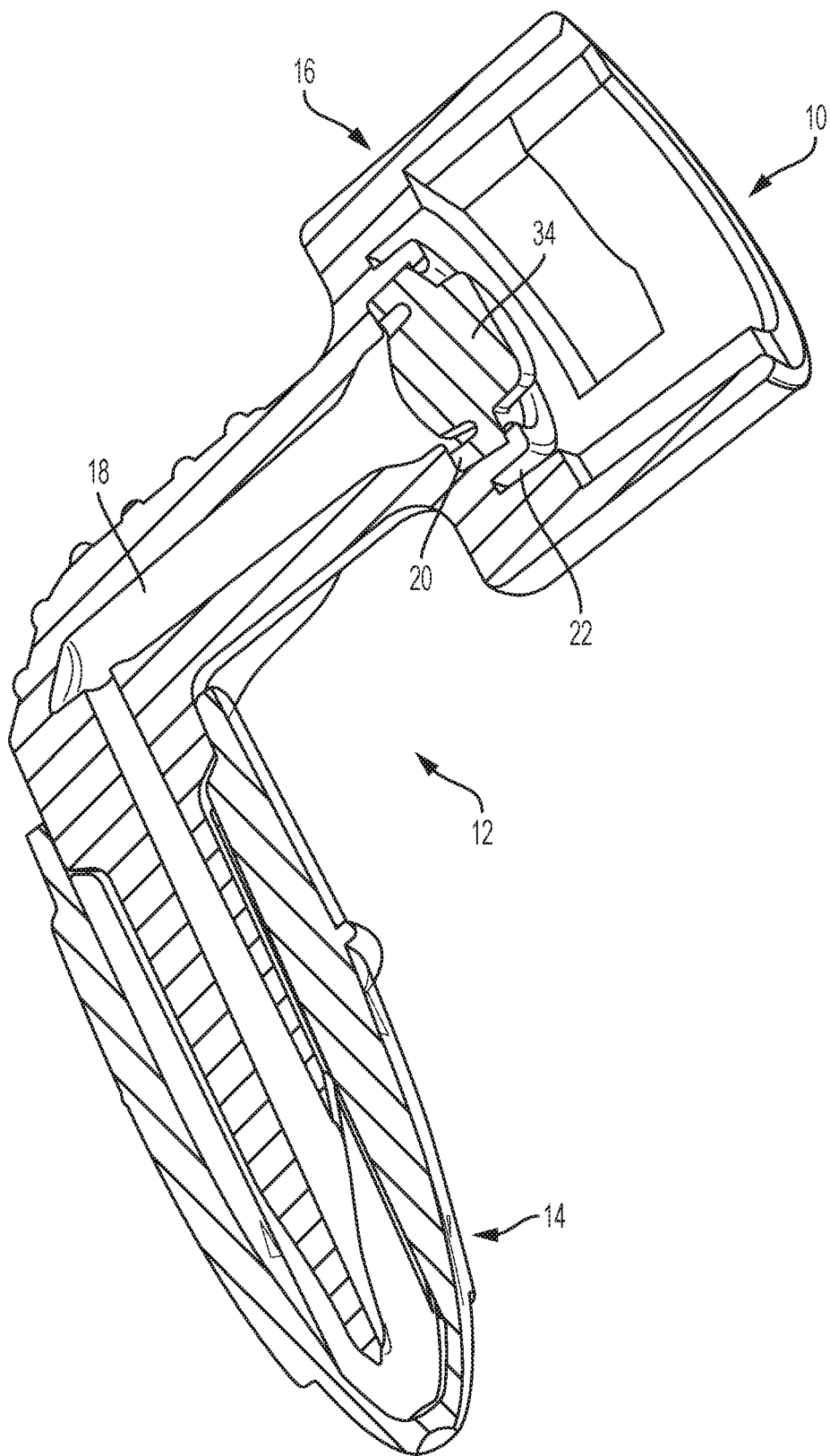
FIG. 2 is a perspective cross-sectional view of a system according to another example of the present invention.

With continued reference to FIGS. 1A-1B, the connector 12 has a distal end 14 configured for connecting to an intravenous line, such as by a luer-type fitting. A proximal end 16 of the connector 12 is configured for connecting to an injector (not shown), such that drugs from the injector may be delivered to a patient. The connector 12 defines a passageway 18 (shown in FIG. 1B) between the distal end 14 and the proximal end 16. The passageway 18 may be substantially linear, such as shown in FIG. 1B. In some examples, such as shown in FIG. 2, the passageway 18 may be L-shaped. In various other examples, the passageway 18 and/or an overall shape of the connector 12 may have any other shape.

The connector 12 further includes a seal arrangement positioned within the passageway 18. The seal arrangement includes a membrane 34. In some examples, the membrane 34 extends across the passageway 18 and is retained axially from moving within the passageway 18. The membrane 34 includes a body 100 having a proximal portion 102 and a distal portion 104.

With reference to FIG. 1B, the membrane 34 is retained within a membrane seat 20 between the distal end 14 and the proximal end 16. The membrane 34 is retained within the membrane seat 20 by a lip 22 that engages at least a portion of the proximal portion 102 of the membrane 34. A needle (not shown) of the injector is configured to extend through the membrane 34 from the proximal portion 102 toward the distal portion 104 during a drug transfer procedure. A distal end of the cannula is configured to pierce the membrane 34 and extend through the membrane 34. The membrane 34 is configured to engage and seal an intermediate portion of the cannula to maintain a sealed and leak-free connection between the connector 12 and the injector. In various examples discussed herein, the membrane 34 has features that are configured to improve the re-sealing qualities after the penetration of the needle. In addition, various examples of the membrane 34, discussed herein, have features that are configured to minimize coring (generation of particles during cannula penetration).

Figure 3A:
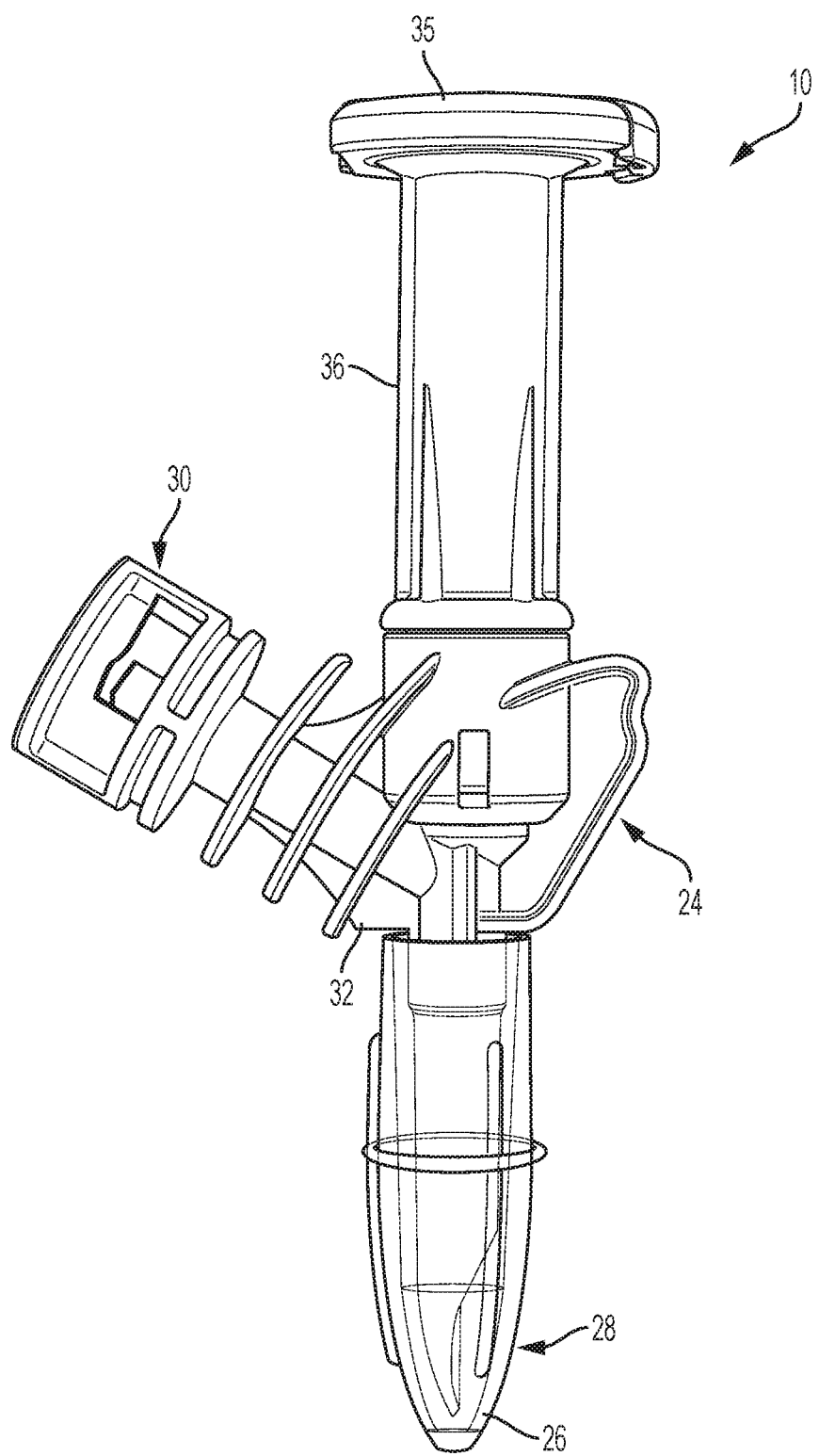
FIG. 3A is a partially perspective front view of a system according to another example of the present invention.
Figure 3B:
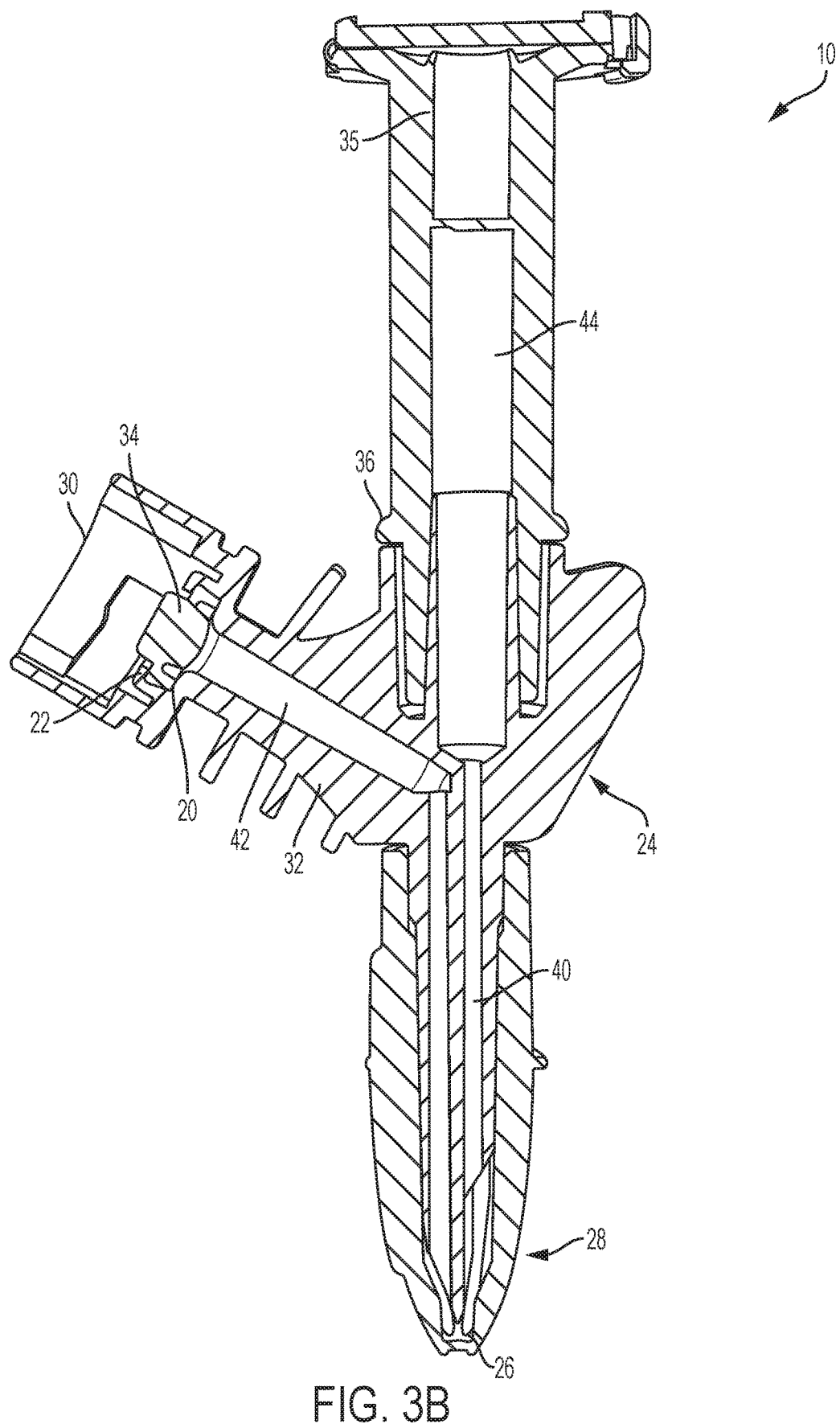
FIG. 3B is a partially perspective front cross-sectional view of the system shown in FIG. 3A.

Referring to FIGS. 3A-3B, one example of a system 10 for the closed transfer of fluids includes an infusion adapter 24 configured to securely connect to an intravenous bag in a leak-proof manner for use in a drug transfer procedure. Various aspects of the infusion adapter 24 are described in U.S. Patent Application Publication No. 2014/0150911, which is hereby incorporated in reference in its entirety. In one example, the infusion adapter 24 has a PhaSeal connector which is compatible with a Becton Dickinson PhaSeal™ System available from Becton, Dickinson and Company of Franklin Lakes, N.J. In other embodiments, the infusion adapter 24 comprises a connector which is compatible with other closed system drug transfer devices.

With continued reference to FIGS. 3A-3B, the infusion adapter 24 includes a connection portion 26 located at a distal end 28, a first port 30 located at a first port end 32, and a second port 35 located at a second port end 36. The connection portion 26 includes an anchor component and a fluid channel 40 (shown in FIG. 3B). With reference to FIG. 3B, the first port 30 includes a first port fluid channel 42 and the second port 35 includes a second port fluid channel 44. The fluid channel 40 of the connection portion 26 is in fluid communication with the first port fluid channel 42 of the first port 30 such that a fluid may flow into the infusion adapter 24 at the first port 30, travel through the first port fluid channel 42 to the fluid channel 40 of the connection portion 26 and out the distal end 28 of the infusion adapter 24. The fluid channel 40 of the connection portion 26 is also in fluid communication with the second port fluid channel 44 of the second port 35 such that a fluid may flow into the infusion adapter 24 at the distal end 28 of the connection portion 26, travel through the fluid channel 40 to the second port fluid channel 44 and out the second port 35 of the infusion adapter 24.

In some examples, the infusion adapter 24 may comprise a generally Y-shape. Further, it is contemplated that the infusion adapter 24 may be made available in a variety of shapes and sizes as long as the first port 30 is spaced a distance from the second port 35 so that the first port 30 may be connected to a syringe assembly containing a medication fluid and the second port 35 may be connected to an intravenous line that is adapted for connection to a bloodstream of a patient. For example, the infusion adapter 24 may comprise a generally T-shape.

With continued reference to FIG. 3B, the infusion adapter 24 further includes a seal arrangement positioned within the first port fluid channel 42. The seal arrangement includes the membrane 34, such as the membrane 34 described herein with reference to FIGS. 1A-1B. In some examples, the membrane 34 extends across the first port fluid channel 42 and is retained axially from moving within the first port fluid channel 42. The membrane 34 is retained within a membrane seat 20 of the first port fluid channel 42. The membrane 34 is retained within the membrane seat 20 by a lip 22 that engages at least a portion of the proximal portion of the membrane 34.

Figure 4A:
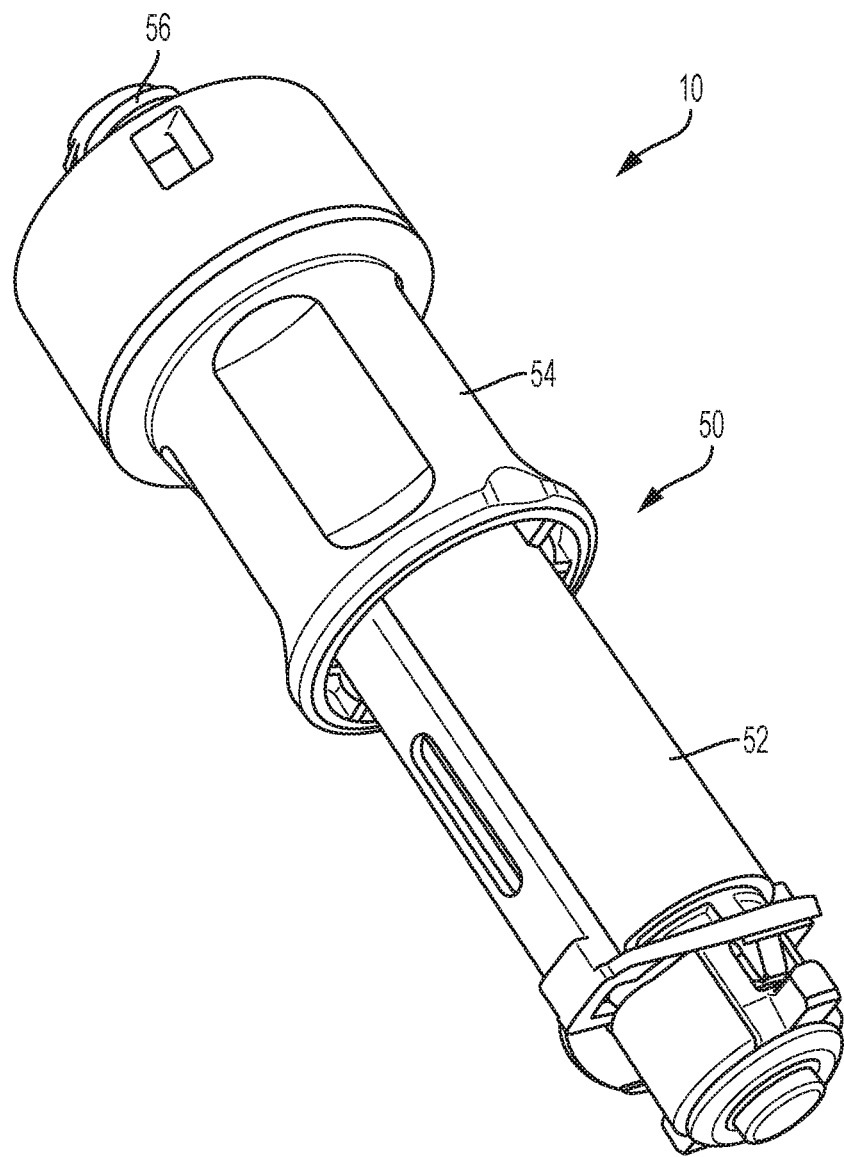
FIG. 4A is a perspective view of a system according to another example of the present invention.
Figure 4B:
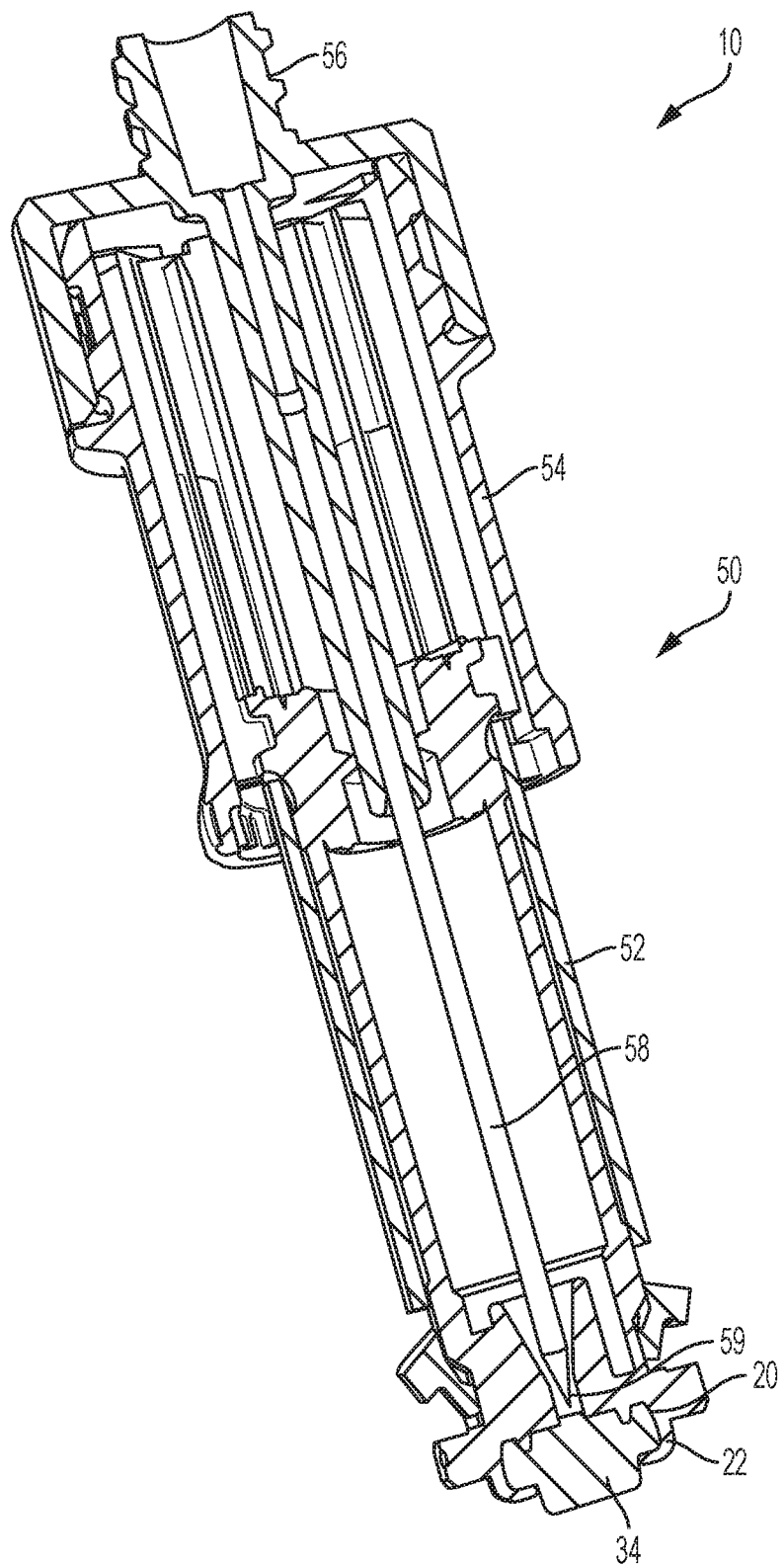
FIG. 4B is a perspective longitudinal cross-sectional view of the system shown in FIG. 4A.

Referring to FIGS. 4A-4B, one example of a system 10 for the closed transfer of fluids includes an injector 50. Various aspects of the injector 50 are described in U.S. Patent Application Publication No. 2014/0150925, which is hereby incorporated in reference in its entirety. In some examples, the injector 50 has a tubular body 52, an outer sleeve 54, and an adapter 56. The injector 50 is configured to establish fluid communication between a first medical container and a second medical container or between a medical container and a further device, such as a vial adapter. Commonly used medical fluid containers, as is known in the art, include syringes, vials, cartridges, fluid containing bags, medical lines, or similar structures and conduits for holding medical fluids such as drugs, solvents, and diluents. The injector 50 is used to establish fluid communication between the containers so that a user may inject fluid from one container to the other or may draw fluid from one container to the other. The injector 50 also includes a structure for locking the device to the first and/or second medical containers and to maintain the connection between the connector and container. Fluid communication between the medical containers is established by moving the outer sleeve 54 from a first position in which a portion of the tubular body 52 extends from the outer sleeve 54, to a second, engaged position in which the outer sleeve 54 encloses the tubular body 52. The tubular body 52 further includes a needle 58 (shown in FIG. 4B) extending longitudinally through the tubular body 52 from its proximal end to the distal end. The needle 58 defines a lumen which provides a fluid path through the tubular body 52. The needle 58 is formed from medical grade metal or other material capable of being sharpened to a tip 59 that is capable of piercing the sealing arrangement, such as the membrane 34. The needle 58 has a first position in which it is entirely enclosed within the tubular body 52 and a second, exposed position where the needle 58 is forced through the membrane 34 and brought into contact with the second medical container or vial adapter.

With reference to FIG. 4B, the membrane 34 extends across the inner cavity of the tubular body 52 and is retained axially from moving within the tubular body 52. The membrane 34 is retained within a membrane seat 20 of the tubular body 52. The membrane 34 is retained within the membrane seat 20 by a lip 22 that engages at least a portion of the proximal portion of the membrane 34.

Figure 5A:
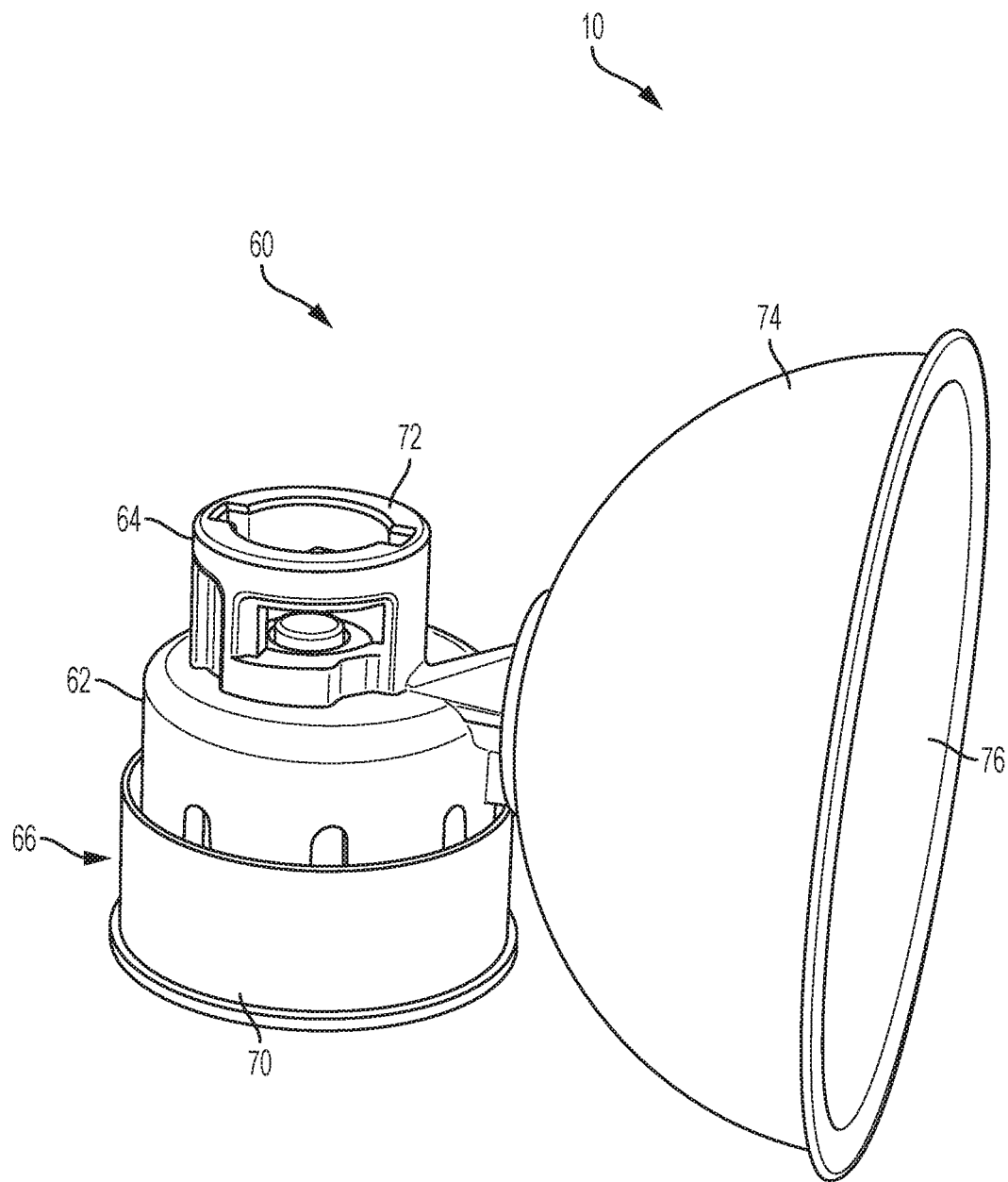
FIG. 5A is a perspective view of a system according to another example of the present invention.
Figure 5B:
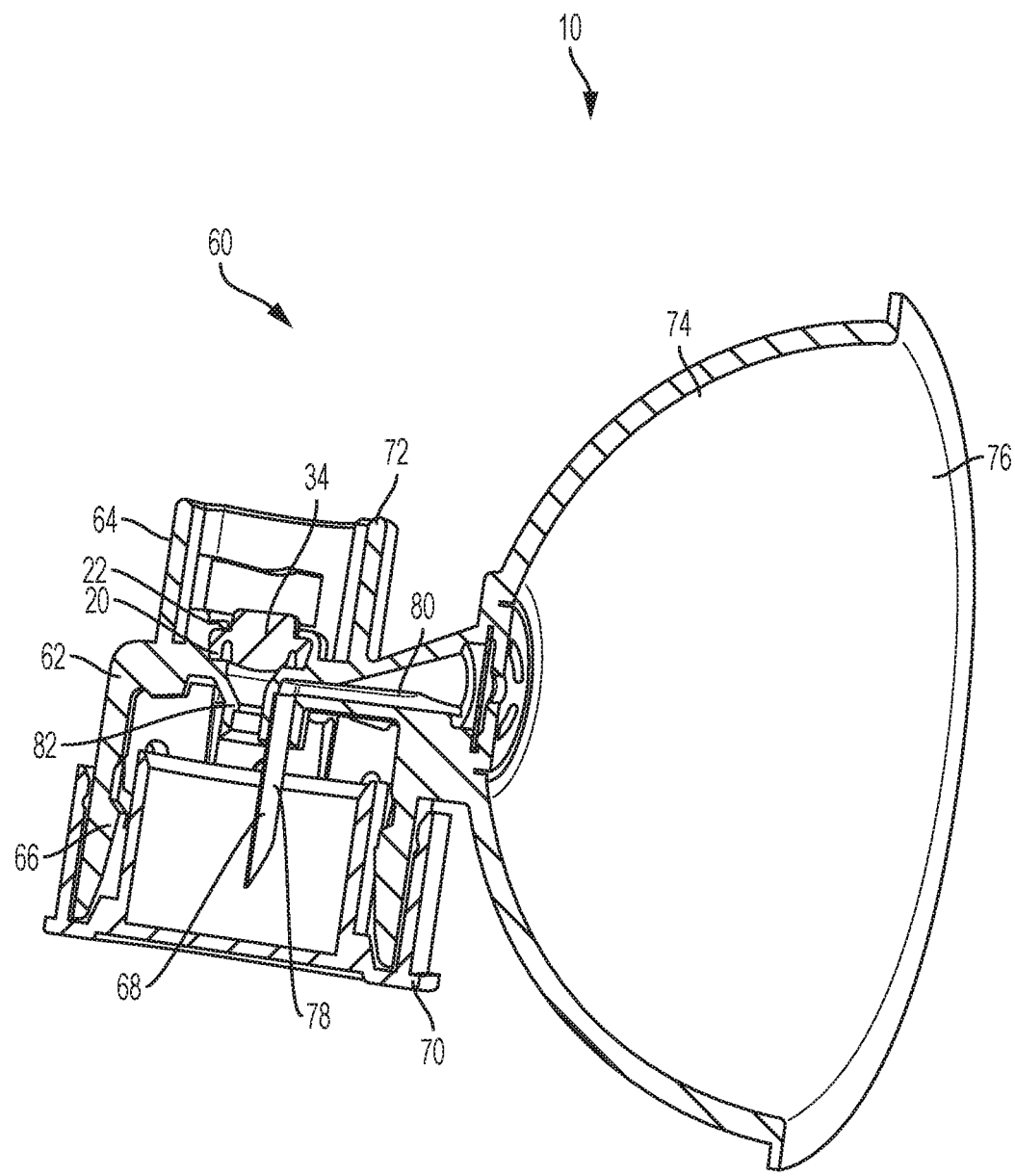
FIG. 5B is a perspective longitudinal cross-sectional view of the system shown in FIG. 5A.
Figure 5C:
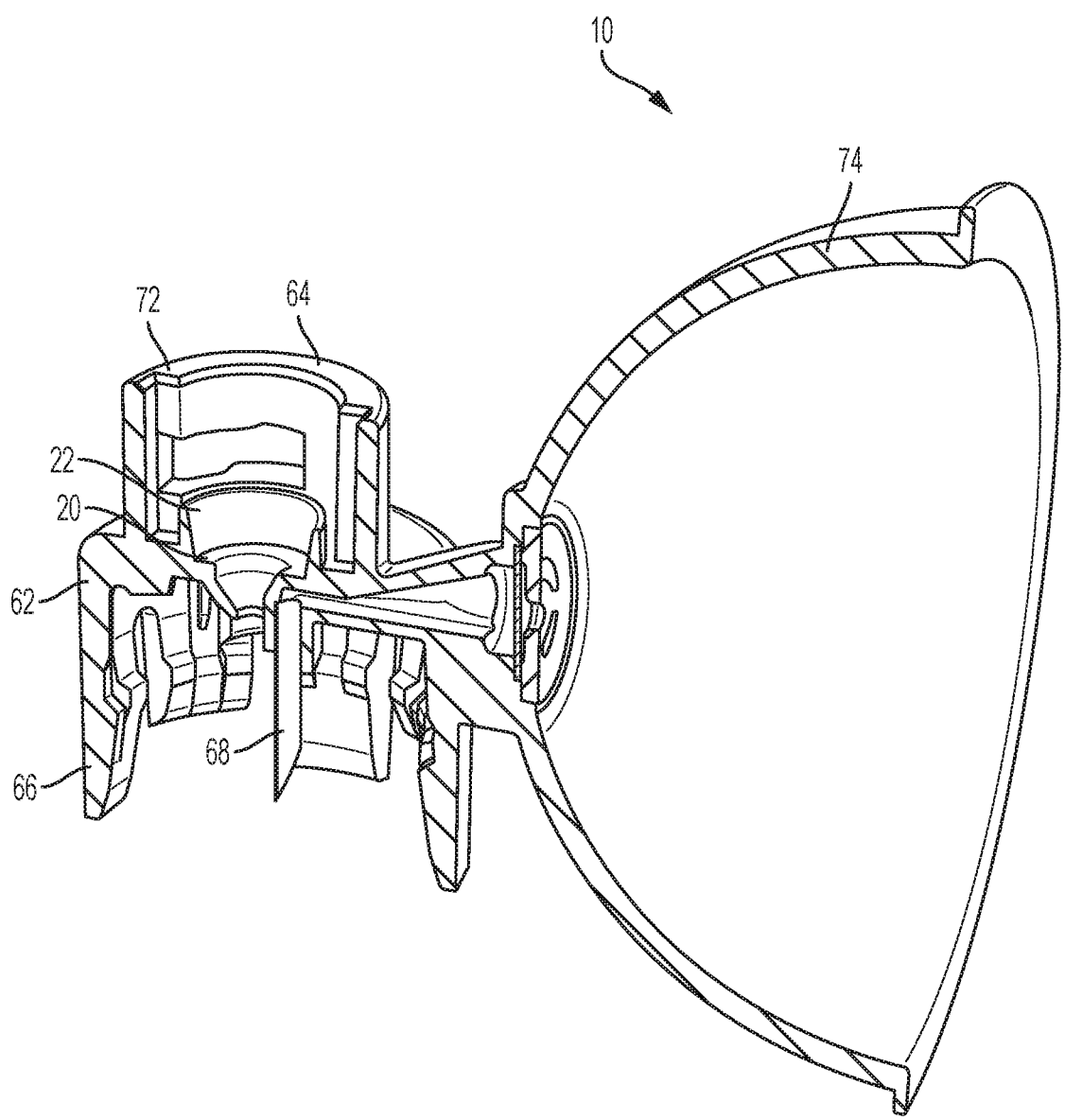
FIG. 5C is a perspective longitudinal cross-sectional view of the system shown in FIG. 5A showing a membrane lip in a first position.

Referring to FIGS. 5A-5B, one example of a system 10 for the closed transfer of fluids includes a protector 60. Various aspects of the protector 60 are described in U.S. Patent Application Publication No. 2015/0082746, which is hereby incorporated in reference in its entirety. In some examples, the protector 60 includes a body 62 having a first side 64 and a second side 66, a piercing member 68 (shown in FIG. 5B) extending from the second side 66 of the body 62, and a removable sleeve 70 surrounding the piercing member 68. The protector 60 is configured to transfer fluid from a fluid container having a sealing member, such as a vial, a bottle, or a bag.

With continued reference to FIGS. 5A-5B, the body 62 includes a first connecting portion 72 extending from the first side 64 of the body 62. The first connecting portion 72 is configured to attach the protector 60 to a syringe adapter or other suitable device or container to allow removal or insertion of fluid into the fluid container. The protector 60 further includes a pressure equalization arrangement 74 that is configured to equalize the pressure within the container during fluid transfer through the use of an expansible chamber 76. The piercing member 68 defines a longitudinal vent channel 78 and a vent opening 80 extending from the distal end of the piercing member 68 toward the proximal end of the piercing member 68. The vent opening 80 is in fluid communication with the longitudinal vent channel 78. The longitudinal vent channel 78 extends through the body 62 of the protector 60 and is in fluid communication with the expansible chamber 76 of the pressure equalization arrangement 74. In particular, during use of the protector 60, the longitudinal vent channel 78 and the pressure equalization arrangement 74 is utilized to regulate the pressure within the fluid container and contains the medicament and any vapor thereof within the protector 60 and within the fluid container. The pressure equalization arrangement 74 may be the balloon or membrane arrangement shown in U.S. Pat. No. 8,523,838, which is hereby incorporated by reference in its entirety, although other suitable pressure equalization arrangements may be utilized, such as, but not limited to, a filtered vent exit.

With reference to FIG. 5B, the protector 60 further includes a longitudinal fluid channel 82 extending through the body 62 and in fluid communication with the first connecting portion 72. The first connecting portion 72 may include a seal arrangement positioned to seal the interior of the first connecting portion 72, such as the longitudinal fluid channel 82. The seal arrangement includes the membrane 34, such as the membrane 34 described herein with reference to FIGS. 1A-1B. The membrane 34 extends across an inner cavity of the first connecting portion 72 and is retained axially from moving within the tubular body 52. The membrane 34 is retained within a membrane seat 20 of the tubular body 52. The membrane 34 is retained within the membrane seat 20 by a lip 22 that engages at least a portion of the proximal portion 102 of the membrane 34. In some examples, the lip 22 is folded over the membrane 34 in a radially inward direction after the membrane 34 engages a distal end of the membrane seat 20. In some examples, the lip 22 is folded over the membrane 34 from a first position (shown in FIG. 5C) to a second position (shown in FIG. 5B) in a radially inward direction after the membrane 34 engages a distal end of the membrane seat 20. In this manner, the membrane 34 can be retained axially. In addition, at least a portion of an outer perimeter of the membrane 34 may be bonded with at least a portion of an inner perimeter of the membrane seat 20 to radially bond the membrane 34. For example, the membrane 34 may be ultrasonically welded to the membrane seat 20.

Figure 6A:
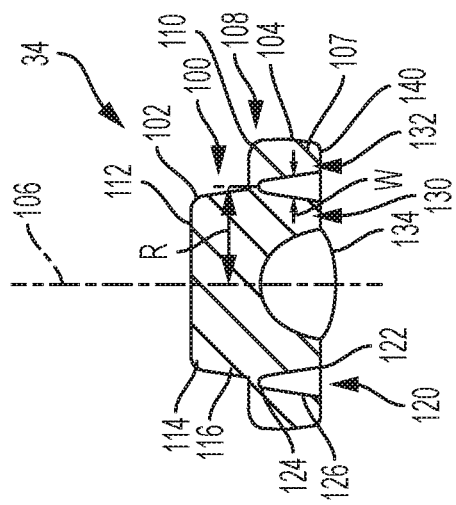
FIG. 6A is a side view of a cannula and a stress resistant membrane in accordance with one example of the present invention.
Figure 6B:
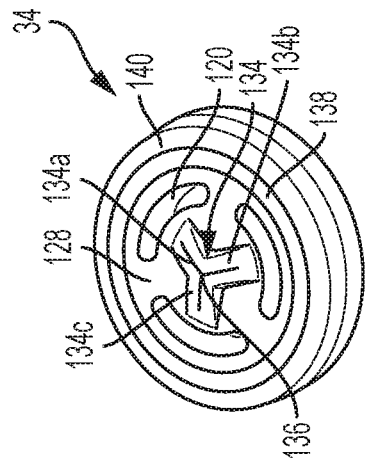
FIG. 6B is a cross-sectional side view of the stress resistant membrane shown in FIG. 6A.

Referring to FIGS. 6A-6B, a membrane 34 is shown in accordance with one example. The membrane 34 includes a body 100 having a proximal portion 102 and a distal portion 104. The proximal portion 102 and the distal portion 104 are monolithically formed together to define the body 100 as a single, unitary structure. In some examples, the proximal portion 102 and the distal portion 104 may be formed separately and subsequently joined together in a separable or non-separable manner. The body 100 is substantially symmetrical about a central axis 106 extending through a central portion of the proximal portion 102 and the distal portion 104. In some examples, the proximal portion 102 and the distal portion 104 may have a substantially circular cross-section across the central axis 106. In various examples, the membrane 34 may be manufactured from an elastomeric material, such as a thermoplastic elastomer material, or isoprene.

With continued reference to FIGS. 6A-6B, the body 100 may have a skirt 107 extending radially outward from the distal portion 104 such that a lip 108 is formed between the proximal portion 102 and the distal portion 104. In some examples, the lip 108 may be defined by a proximal surface 110 of the distal portion 104. The lip 108 defines an engagement surface such that the body 100 of the membrane 34 can engage at least a portion of the system 10, such as at least a portion of the membrane seat 20. In some examples, the lip 108 may be substantially perpendicular relative to the central axis 106. In other examples, the lip 108 may be angled at a non-orthogonal angle relative to the central axis 106. The lip 108 may have a planar surface, a non-planar surface, or a combination thereof.

A proximal surface 112 of the proximal portion 102 may have a dome-shaped or convex surface with its apex aligned with the central axis 106. In other examples, the proximal surface 112 of the proximal portion 102 may have a substantially planar surface or a frusto-conical surface. In further examples, the proximal surface 112 of the proximal portion 102 may have a non-planar surface comprised of one or more linear and/or non-linear sections. The outer perimeter of the proximal surface 112 of the proximal portion 102 may have a radiused edge 114 that transitions to a sidewall 116 of the proximal portion 102. The sidewall 116 is joined with the proximal surface 110 of the distal portion 104. The proximal portion 102 and the distal portion 104 may be aligned coaxially such that the central axis 106 extends through a center of both portions. In some examples, a central axis of the proximal portion 102 may be offset relative to a central axis of the distal portion 104.

Figure 6C:
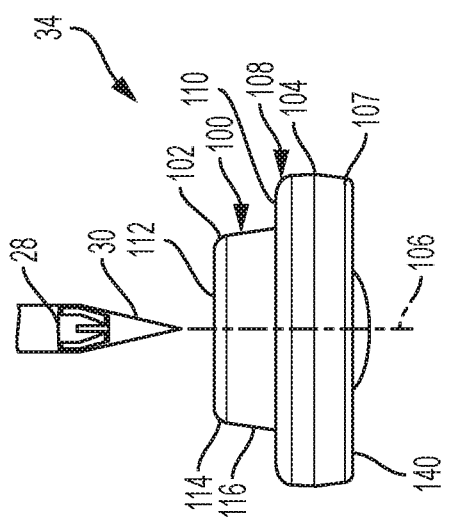
FIG. 6C is a bottom perspective view of the stress resistant membrane shown in FIG. 6A.
Figure 6D:
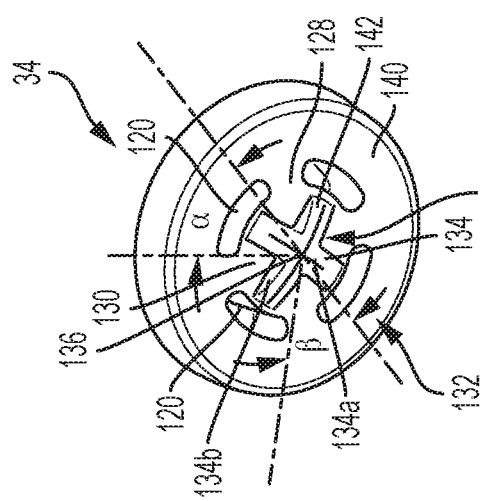
FIG. 6D is a bottom perspective view of a stress resistant membrane in accordance with another example of the present invention.

With reference to FIGS. 6B-6D, the distal portion 104 may have at least one well 120 recessed in a proximal direction from a distal surface 140 of the distal portion 104. Referring to FIG. 6B, the at least one well 120 may be formed as a channel that is recessed into the body of the distal portion 104. The at least one well 120 has a first end 122 separated from a second end 124 by a pair of sidewalls 126. In some examples, the first end 122 is open, while the second end 124 is closed. The sidewalls 126 are spaced apart from each other by a distance W, which defines a width of the at least one well 120.

In some examples, the at least one well 120 may be continuous in a circumferential direction about the central axis 106 at a radius R away from the central axis 106 to define an annular shape. In other examples, the at least one well 120 may have a continuous, non-circular shape, such as an oval shape, rectangular shape, or other polygonal shape. A plurality of continuous wells 120 may be provided at different radii away from the central axis 106. In other examples, the at least one well 120 may extend over a portion of a full circumference about the central axis 106 at a radius R away from the central axis 106. In this manner, terminal ends of the well 120 are separated from each other by the body of the distal portion 104 to define an interrupted annular shape. In other examples, the at least one well 120 may have an interrupted, non-circular shape, such as an interrupted oval shape, rectangular shape, or other polygonal shape.

In further examples, a plurality of wells 120 may be provided. All of the wells 120 may be provided at a same radius R away from the central axis 106. In some examples, at least one of the plurality of wells 120 may be provided at a radius that is larger or smaller than the radius R of the remaining wells 120. With reference to FIGS. 6C-6D, each of the plurality of wells 120 may extend over an angular extension α of a full circumference about the central axis 106 to define a length of the well 120. The wells 120 may have an equal or unequal angular extension α. Each of the plurality of wells 120 may be separated from adjoining wells 120 by a connecting rib 128. Each connecting rib 128 may have an equal or unequal angular extent between adjacent wells 120. In other examples, at least one well 120 may have an unequal angular extension β between adjacent wells 120. The connecting ribs 128 bridge the gap between a central portion 130 of the body 100 and an outer portion 132 of the body 100 due to the presence of one or more wells 120. In this manner, dimensional stability of the membrane body 100 is retained after the cannula, such as the needle 58 shown in FIG. 4B, is retracted from the membrane 34.

In various examples, the at least one well 120 is configured to reduce compression of the membrane 34 in certain circumstances, such as during ultrasonic welding of the membrane 34 with at least one component of the system 10. Without intending to be bound by theory, it has been found through experimentation that ultrasonic welding of the membrane 34 with the housing 16 may result in a localized compression of the membrane material within the membrane body 100, thereby affecting how easily the needle 58 can penetrate the membrane 34. The at least one well 120 isolates the central portion 130 of the body 100 from the outer portion 132 that radially surrounds the central portion 130 by creating a space therebetween. In this manner, any material compression that may occur due to welding of an outer periphery of the membrane 34 will be localized to the outer portion 132 without affecting the central portion 130. Thus, the needle 58 can freely penetrate the body 100 of the membrane 34. In addition, the at least one well 120 allows for a radial expansion of the central portion 130 during penetration of the needle 58 without a corresponding expansion of the outer portion 132. In this manner, the at least one well 120 absorbs the deformation of the central portion 130 of the membrane 34 to minimize or eliminate coring during penetration of the needle 58.

With reference to FIGS. 6C-6D, the membrane 34 has at least one slit 134 extending through at least a portion of the body 100. In some examples, the at least one slit 134 extends through at least a portion of the distal portion 104 of the body 100 in a direction along the central axis 106 (shown in FIGS. 6A-6B). In other examples, the at least one slit 134 extends through the entire distal portion 104 of the body 100 and at least a portion of the proximal portion 102 in a direction along the central axis 106. In further examples, the at least one slit 134 extends through the entire body 100 of the membrane 34 in a direction along the central axis 106. The axial extent of the at least one slit 134 in a direction along the central axis 106 reduces the length that the distal end 30 of the needle 58 must penetrate through the body 100 of the membrane 34, thereby reducing or eliminating the possibility of coring (removal of material from the body 100 of the membrane 34).

The at least one slit 134 is desirably oriented such that the needle 58 penetrates through the slit 134 during insertion of the needle 58 through the membrane 34. For example, the needle 58 may partition the at least one slit 134 as the needle 58 is inserted through the membrane 34 by flexing the body 100 of the membrane 34 into an open position. After withdrawing the needle 58 from the membrane 34, the at least one slit 134 is configured to close back to its original position without any deformation of the body 100 of the membrane 34. In this manner, the at least one slit 134 creates a hydraulic seal to prevent passage of liquid or gas through the membrane 34. In some examples, such as shown in FIG. 6B, the at least one slit 134 may be substantially linear, curved, or a combination thereof, such that the slit 134 bisects the central portion 130 in half at the location of the slit 134. The slit 134 may have a rounded shape when viewed in a cross-sectional plane of the membrane 34 along the central axis 106. In some examples, the slit 134 may be positioned on a raised area 142 that protrudes distally from a distal surface 140 of the distal portion 104. The raised area 142 may have an arcuate shape with an apex intersecting the central axis 106. The shape of the raised area 142 desirably corresponds to the shape of the slit 134. For example, for a linearly shaped slit 134, the raised area 142 may also be linear along its longitudinal length with an arcuate cross-sectional profile in a plane parallel to the plane of the central axis 106.

With reference to FIG. 6C, the at least one slit 134 may be substantially cross-shaped with a pair of slits 134a, 134b intersecting at an approximate midpoint thereof. The pair of slits 134a, 134b may be oriented at substantially right angles relative to each other, or the pair of slits 134a, 134b may intersect at acute or obtuse angles. Each slit 134a, 134b may extend through at least a portion of the distal portion 104 of the body 100 in a direction along the central axis 106. Each slit 134a, 134b may be substantially linear, curved, or a combination thereof. The slits 134a, 134b are desirably oriented such that the needle 58 penetrates through an intersection point 136 of the pair of slits 134a, 134b during insertion of the needle 58 through the membrane 34.

With reference to FIG. 6D, the at least one slit 134 may be substantially Y-shaped with three individual slits 134a, 134b, 134c connected to one another at one of their end points. The slits 134a, 134b, 134c may be oriented such that the slits 134a, 134b, 134c intersect at equal or unequal angles therebetween. Each slit 134a, 134b, 134c may extend through at least a portion of the distal portion 104 of the body 100 in a direction along the central axis 106. Each slit 134a, 134b, 134c may be substantially linear, curved, or a combination thereof. The slits 134a, 134b, 134c are desirably oriented such that the needle 58 penetrates through an intersection point 136 of the slits 134a, 134b, 134c during insertion of the needle 58 through the membrane 34.

With continued reference to FIG. 6D, the membrane 34 may have a retention ring 138 that protrudes distally from a distal surface 140 of the distal portion 104. The retention ring 138 is configured to maintain the membrane 34 in its position within the housing 16. The retention ring 138 is shaped to engage a corresponding groove (not shown) on the housing 16. For example, the retention ring 138 may have a substantially semi-circular shape in cross section taken along a plane extending in a direction of the central axis 106.

With continued reference to FIG. 6D, the retention ring 138 may be formed as a continuous ring centered around the central axis 106. In some examples, the retention ring 138 may be discontinuous, such that it does not fully extend around the central axis 106. In further examples, the retention ring 138 may be segmented, such that the retention ring 138 is comprised of two or more disconnected segments.

With reference to FIGS. 7A-7E, the membrane 34 is shown in accordance with various examples. The components of the membrane 34 shown in FIGS. 7A-7E are substantially similar to the components of the membrane 34 described herein with reference to FIGS. 6A-6D. Reference numerals in FIGS. 7A-7E are used to illustrate identical components of the corresponding reference numerals in FIGS. 6A-6D. As the previous discussion regarding the membrane 34 generally shown in FIGS. 6A-6D is applicable to the aspect of the present disclosure shown in FIGS. 7A-7E, only the relative differences between the membrane 34 generally shown in FIGS. 6A-6D and the membrane 34 generally shown in FIGS. 7A-7E are discussed hereinafter.

The membrane 34 in the examples shown in FIGS. 7A-7E has the body 100 with the proximal portion 102 and the distal portion 104 monolithically formed together and symmetrical about the central axis 106. In each example, the distal portion 104 has a skirt 107 such that a lip 108 is formed between the proximal portion 102 and the distal portion 104 as a substantially planar surface. The proximal surface 112 of the proximal portion 102 has a substantially planar surface with the radiused edge 114 that transitions to the sidewall 116 of the proximal portion 102. The distal surface 140 of the distal portion 104 is substantially planar (FIGS. 7B-7D), or curved (FIG. 7A). In each example, the membrane 34 has at least one slit 134 extending through the body 100 of the membrane 34 in a direction along the central axis 106.

In each example shown in FIGS. 7A-7D, the distal portion 104 has a well 120 recessed in a proximal direction from a distal surface 140 of the distal portion 104. The well 120 has a first end 122 separated from a second end 124 by a pair of sidewalls 126. With reference to FIGS. 7A-7B, the second end 124 is rounded while the sidewalls 126 are curved such that the width W between the sidewalls 126 changes (i.e., increases or decreases) in a direction from the first end 122 toward the second end 124.

With reference to FIGS. 7C-7D, the second end 124 of the well 120 is angled such that the second end 124 tapers toward the central axis 106 in a distal-to-proximal direction. The pair of sidewalls 126 has a first sidewall 126a and a second sidewall 126b, with the first sidewall 126a extending in a direction substantially parallel to a direction of the central axis 106, and the second sidewall 126b extending at an angle relative to the first sidewall 126a such that the second sidewall 126b tapers away from the central axis 106 in a distal-to-proximal direction. The central portion 130 of the distal portion 104 can be co-planar with the outer portion 132 (FIG. 7C) or recessed in a proximal direction relative to the outer portion 132 (FIG. 7D). With reference to FIG. 7E, the well 120 is substantially V-shaped with the second end 124 positioned at a central portion of the membrane 34 and aligned with the central axis 106. The sidewalls 126 have a plurality of linear segments.

With reference to FIGS. 8A-8D, the membrane 34 is shown in accordance with additional examples. In each example, the distal portion 104 of the membrane 34 may have at least one well 120 recessed in a proximal direction from a distal surface 140 of the distal portion 104. For example, the at least one well 120 may be formed as a channel that is recessed into the body of the distal portion 104.

Figure 8A:
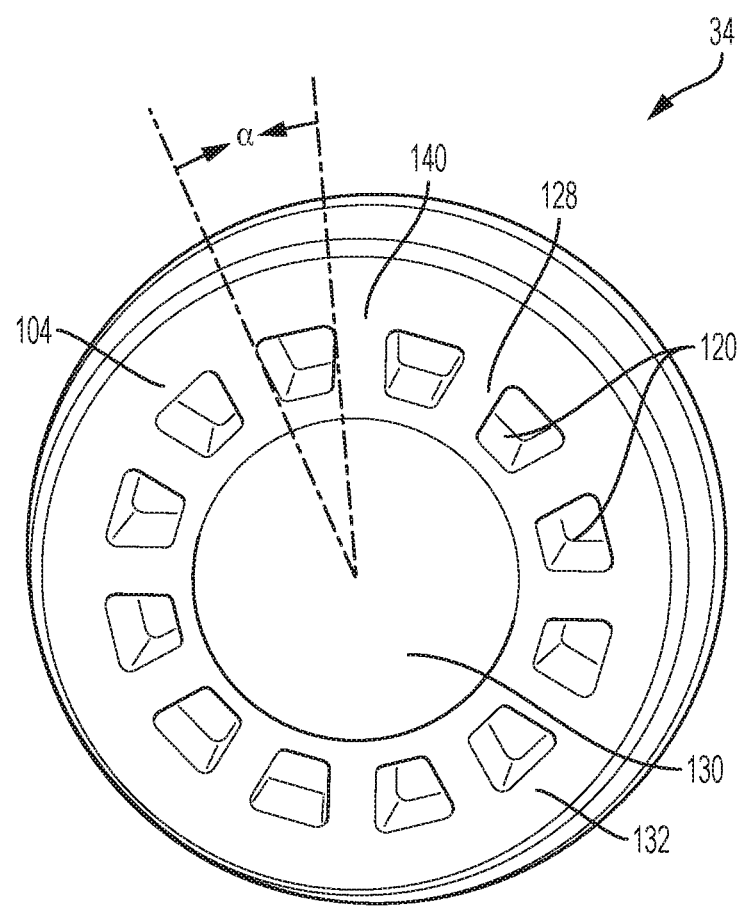
FIG. 8A is a bottom perspective view of a stress resistant membrane in accordance with another example of the present invention.
Figure 8B:
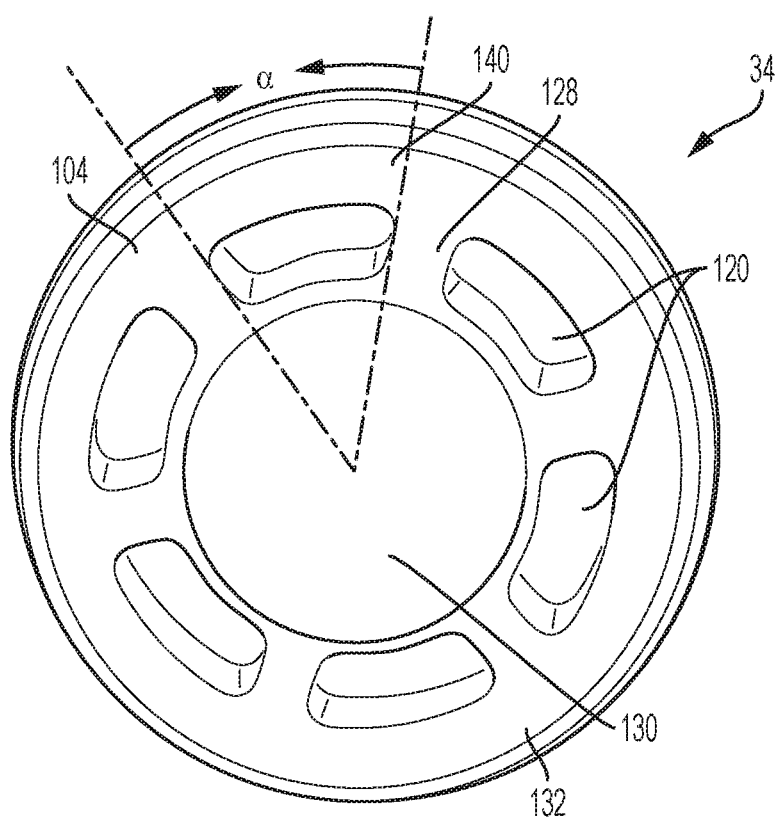
FIG. 8B is a bottom perspective view of a stress resistant membrane in accordance with another example of the present invention.
Figure 8C:
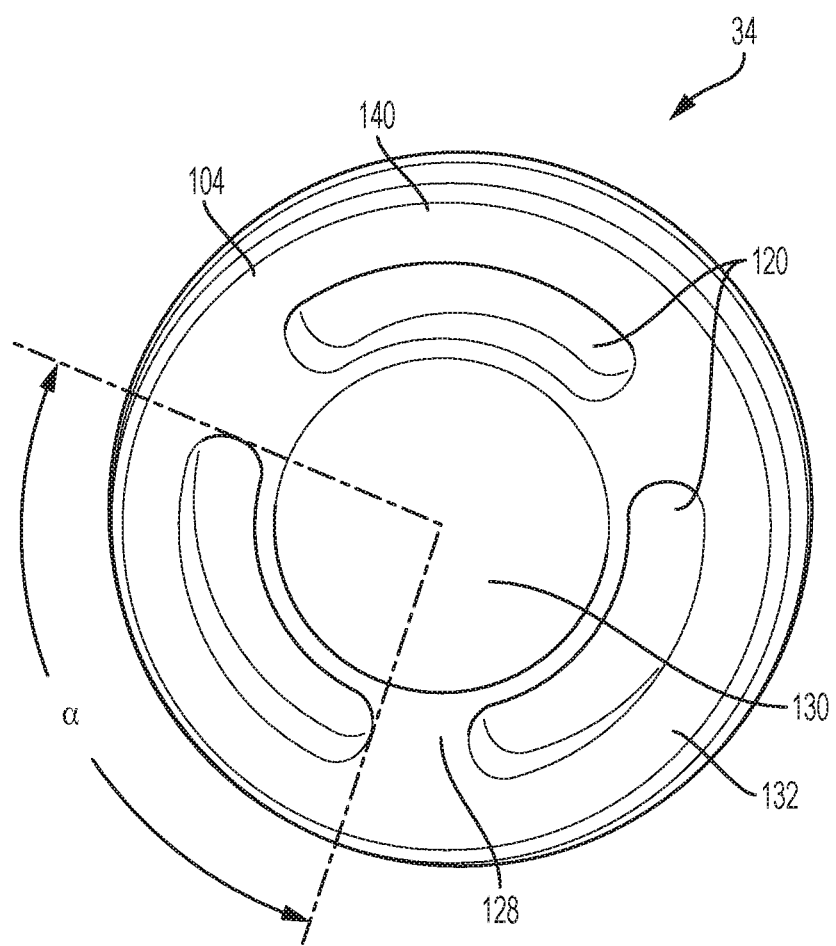
FIG. 8C is a bottom perspective view of a stress resistant membrane in accordance with another example of the present invention.
Figure 8D:
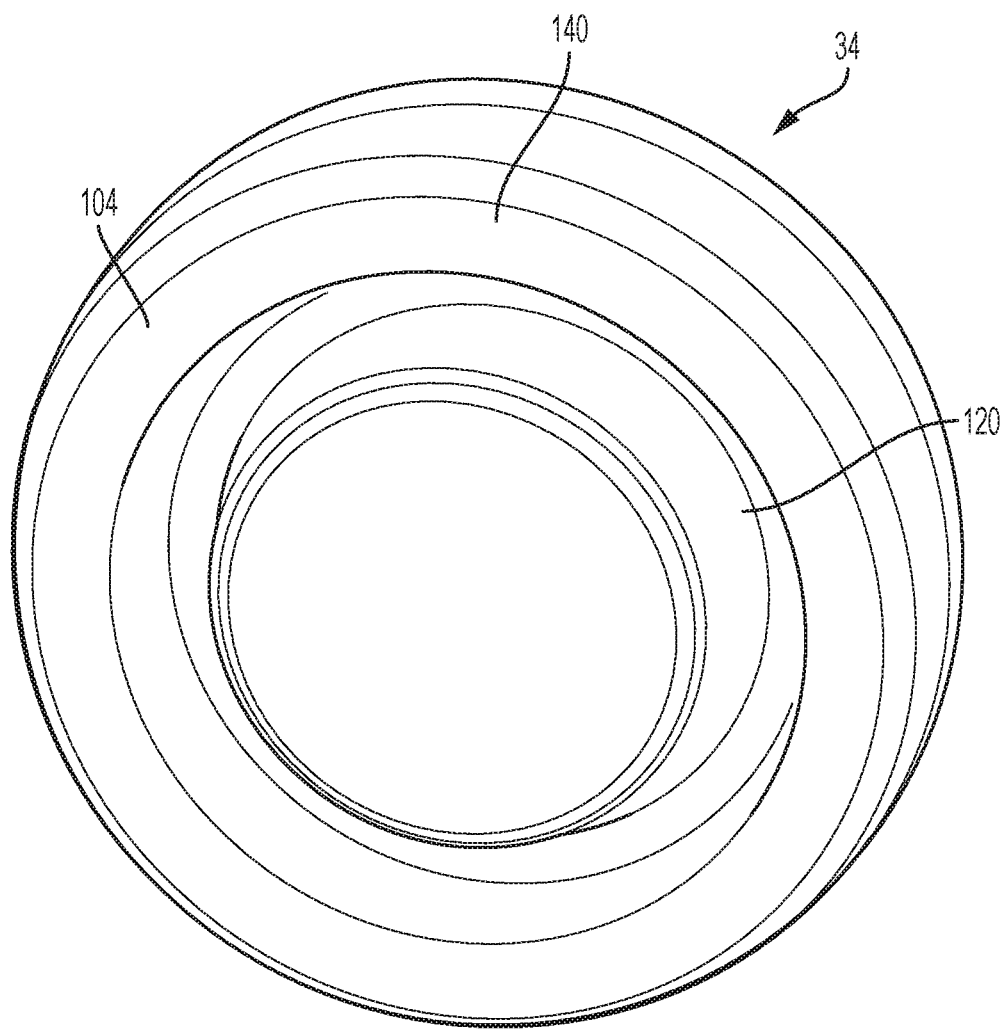
FIG. 8D is a bottom perspective view of a stress resistant membrane in accordance with another example of the present invention.

In some examples, such as shown in FIG. 8D, the at least one well 120 may be continuous in a circumferential direction about the central axis 106 (shown in FIG. 6B) at a radius R away from the central axis 106 to define an annular shape. In other examples, such as shown in FIGS. 8A-8C, the at least one well 120 may extend over a portion of a full circumference about the central axis 106 at a radius R away from the central axis 106. In this manner, terminal ends of the well 120 are separated from each other by the body of the distal portion 104 to define an interrupted annular shape. In the examples shown in FIGS. 8A-8C, all of the wells 120 are provided at a same radius R away from the central axis 106. With reference to FIGS. 8A-8C, each of the plurality of wells 120 may extend over an angular extension α of a full circumference about the central axis 106 to define a length of the well 120. The wells 120 may have an equal or unequal angular extension α. Each of the plurality of wells 120 may be separated from adjoining wells 120 by a connecting rib 128. The connecting ribs 128 bridge the gap between a central portion 130 of the body 100 and an outer portion 132 of the body 100 due to the presence of one or more wells 120. In this manner, dimensional stability of the membrane body 100 is retained after the cannula, such as the needle 58 shown in FIG. 4B, is retracted from the membrane 34.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as they come within known or customary practice in the art to which this disclosure pertains and which fall within the limits of the appended claims.

What is claimed is:

1. A membrane for sealing an open passageway in connection with a closed system transfer device, the closed system transfer device comprising a distal end and a proximal end connected by the passageway, the membrane comprising:

a body having a proximal portion opposite a distal portion along a central axis, the proximal portion comprising a planar portion extending substantially perpendicular with respect to the central axis, the planar portion having an edge that transitions to a sidewall extending substantially parallel with the central axis, the sidewall being joined with a proximal surface of the distal portion, wherein the planar portion has a diameter defined by the sidewall and the planar portion comprises one of a planar surface extending across the diameter and a convex surface having an apex aligned with the central axis;

a skirt extending radially outward from the distal portion such that a lip is formed at a transition between the proximal portion and the distal portion, the lip comprising a planar surface continuously extending from the sidewall of the proximal portion to an outer edge of the skirt, the lip defining a proximal engagement surface configured for engagement with a seat lip, the skirt having a distal engagement surface, wherein the distal engagement surface is oppositely disposed from the proximal engagement surface at a distalmost end of the skirt relative to a vertical axis extending through the body, the distalmost end of the skirt of the distal engagement surface configured for engagement with a membrane seat of the closed system transfer device to retain the membrane in place to seal the open passageway and prevent axial movement of the membrane into the open passageway;

at least one well recessed in the distal portion and extending from a distal end of the distal portion in a proximal direction, thereby forming a channel within the distal portion, the channel having an open first end, a closed second end, and a pair of sidewalls extending between the open first end and the closed second end, wherein the distalmost end of the skirt is defined by the channel and the outer edge of the skirt such that one of the pair of sidewalls comprises the skirt, and wherein the channel is configured to absorb deformation of a central portion of the body, wherein the second end of the channel is rounded and the pair of sidewalls are curved such that a width W between the sidewalls changes in a direction from the first end toward the second end or wherein the pair of sidewalls comprises a first sidewall and a second sidewall with the first sidewall extending in a direction substantially parallel to a direction of the central axis and the second sidewall extending at an angle relative to the first sidewall such that the second sidewall tapers away from the central axis in a distal-to-proximal direction; and at least one slit extending through at least a portion of the body in a direction of a plane aligned along or parallel to the central axis.

2. The membrane of claim 1, wherein the at least one well is continuous in a circumferential direction about the central axis.

3. The membrane of claim 1, wherein the at least one well is discontinuous in a circumferential direction about the central axis.

4. The membrane of claim 1, wherein the at least one well has an annular shape.

5. The membrane of claim 1, wherein the at least one well comprises a plurality of wells.

6. The membrane of claim 1, wherein the at least one well comprises a plurality of wells positioned at a same radius away from the central axis and separated from each other by at least one connecting rib.

7. The membrane of claim 1, wherein the at least one slit extends through at least a portion of the distal portion of the body in a direction along the central axis.

8. The membrane of claim 1, wherein the at least one slit is configured to be opened by a cannula during penetration of the cannula through the membrane and to close upon withdrawal of the cannula from the membrane.

9. The membrane of claim 1, wherein the at least one slit is positioned on a raised area that protrudes distally from the distal portion of the distal end.

10. The membrane of claim 9, wherein the raised area is arcuately shaped with an apex at the central axis of the membrane.

11. The membrane of claim 1, wherein the at least one slit is a pair of slits intersecting each other at a midpoint of each slit.

12. The membrane of claim 11, wherein the pair of slits intersect at a perpendicular angle.

13. The membrane of claim 11, wherein the slits are arranged such that a cannula penetrates the slits through an intersection point of the slits.

14. The membrane of claim 1, wherein the at least one slit is three slits connected to one another at one of their end points.

15. The membrane of claim 1, further comprising a retention ring protruding in a distal direction from the distal portion of the distal end.

16. The membrane of claim 15, wherein the retention ring is continuous in a circumferential direction about the central axis.

17. The membrane of claim 15, wherein the retention ring has an annular shape.

18. The membrane of claim 1, wherein the proximal portion and the distal portion are monolithically formed together.

19. The membrane of claim 1, wherein the body is symmetrical about the central axis.

20. The membrane of claim 1, wherein the lip is substantially perpendicular to the central axis.

21. The membrane of claim 1, wherein the distal end of the distal portion has a convex surface.

22. The membrane of claim 1, wherein the distal end of the distal portion has a planar surface.

23. The membrane of claim 1, wherein an outer perimeter of the proximal portion has a radiused edge.

24. A membrane for sealing an open passageway in combination with a closed system transfer device, the closed system transfer device comprising a distal end and a proximal end connected by the passageway, a seat lip, and a membrane seat, the membrane comprising:

a body having a proximal portion opposite a distal portion along a central axis, the proximal portion comprising a planar portion extending substantially perpendicular with respect to the central axis, the planar portion having an edge that transitions to a sidewall extending substantially parallel with the central axis, the sidewall being joined with a proximal surface of the distal portion;

a skirt extending radially outward from the distal portion such that a lip is formed at a transition between the proximal portion and the distal portion, the lip comprising a planar surface continuously extending from the sidewall of the proximal portion to an outer edge of the skirt, the lip defining a proximal engagement surface engaged with the seat lip of the transfer device, the skirt having a distal engagement surface, wherein the distal engagement surface is oppositely disposed from the proximal engagement surface at a distalmost end of the skirt relative to a vertical axis extending through the body, the distalmost end of the skirt of the distal engagement surface engaged with the membrane seat of the closed system transfer device to retain the membrane in place to seal the open passageway and prevent axial movement of the membrane into the open passageway;

at least one well recessed in the distal portion and extending from a distal end of the distal portion in a proximal direction, thereby forming a channel within the distal portion, the channel having an open first end, a closed second end, and a pair of sidewalls extending between the open first end and the closed second end, wherein the distalmost end of the skirt is defined by the channel and the outer edge of the skirt such that one of the pair of sidewalls comprises the skirt, and wherein the channel is configured to absorb deformation of a central portion of the body, wherein the second end of the channel is rounded and the pair of sidewalls are curved such that a width W between the sidewalls changes in a direction from the first end toward the second end or wherein the pair of sidewalls comprises a first sidewall and a second sidewall with the first sidewall extending in a direction substantially parallel to a direction of the central axis and the second sidewall extending at an angle relative to the first sidewall such that the second sidewall tapers away from the central axis in a distal-to-proximal direction; and at least one slit extending through at least a portion of the body in a direction of a plane aligned along or parallel to the central axis, wherein the seat lip is folded over the membrane in a radially inward direction, and wherein the membrane seat and seat lip comprises a single continuous member that prevents axial movement of the membrane within the closed system transfer device.

25. A membrane for sealing an open passageway in combination with a closed system transfer device, the closed system transfer device comprising a distal end and a proximal end connected by the passageway, and a membrane seat, the membrane comprising:

a body having a proximal portion opposite a distal portion along a central axis, the proximal portion comprising a top portion extending substantially perpendicular with respect to the central axis, the top portion having an edge that transitions to a sidewall extending substantially parallel with the central axis, the sidewall being joined with a proximal surface of the distal portion;

a skirt extending radially outward from the distal portion such that a lip is formed at a transition between the proximal portion and the distal portion, the lip comprising a planar surface continuously extending from the sidewall of the proximal portion to an outer edge of the skirt, the skirt defining an engagement surface at a distalmost end of the skirt, the engagement surface engaged with the membrane seat of the closed system transfer device to prevent axial movement of the membrane;

at least one well recessed in the distal portion and extending from a distal end of the distal portion in a proximal direction, thereby forming a channel within the distal portion, the channel having an open first end, a closed second end, and a pair of sidewalls extending between the open first end and the closed second end, wherein the distalmost end of the skirt is defined by the channel and the outer edge of the skirt such that one of the pair of sidewalls comprises the skirt, said pair of sidewalls forming an open portion in the well, wherein the open portion extends from one of the pair of sidewalls to another one of the pair of sidewalls, the open portion configured to allow for radial expansion of a central portion defined by one of the pair of sidewalls without a corresponding expansion of the other one of the pair of sidewalls to minimize or eliminate coring during penetration of the membrane, wherein the second end of the channel is rounded and the pair of sidewalls are curved such that a width W between the sidewalls changes in a direction from the first end toward the second end or wherein the pair of sidewalls comprises a first sidewall and a second sidewall with the first sidewall extending in a direction substantially parallel to a direction of the central axis and the second sidewall extending at an angle relative to the first sidewall such that the second sidewall tapers away from the central axis in a distal-to-proximal direction; and at least one slit extending through at least a portion of the body in a direction of a plane aligned along or parallel to the central axis, wherein the membrane is configured to extend across and seal the open passageway within the closed system transfer device, and wherein the membrane seat retains the membrane from axially moving into the open passageway.

* * * * *